United States Patent
Dyballa et al.

(10) Patent No.: US 9,790,244 B2
(45) Date of Patent: Oct. 17, 2017

(54) BISPHOSPHITES HAVING AN UNSYMMETRIC OUTER BIPHENOL UNIT

(71) Applicants: Katrin Marie Dyballa, Recklinghausen (DE); Robert Franke, Marl (DE); Dirk Fridag, Haltern am See (DE); Armin Boerner, Rostock (DE); Detlef Selent, Rostock (DE)

(72) Inventors: Katrin Marie Dyballa, Recklinghausen (DE); Robert Franke, Marl (DE); Dirk Fridag, Haltern am See (DE); Armin Boerner, Rostock (DE); Detlef Selent, Rostock (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/954,339

(22) Filed: Nov. 30, 2015

(65) Prior Publication Data

US 2016/0159840 A1 Jun. 9, 2016

(30) Foreign Application Priority Data

Dec. 4, 2014 (EP) ..................................... 14196187

(51) Int. Cl.
    *C07B 41/06* (2006.01)
    *C07C 45/50* (2006.01)
    *B01J 31/18* (2006.01)
    *C07F 9/6574* (2006.01)

(52) U.S. Cl.
CPC ......... *C07F 9/65746* (2013.01); *B01J 31/185* (2013.01); *C07B 41/06* (2013.01); *C07C 45/50* (2013.01); *B01J 2231/321* (2013.01); *B01J 2531/822* (2013.01)

(58) Field of Classification Search
CPC .... C07C 45/50; C07C 47/02; B01J 2231/321; B01J 2531/822; B01J 31/185; C07B 41/06; C07F 9/65746
See application file for complete search history.

(56) References Cited

U.S. PATENT DOCUMENTS

| | | | | |
|---|---|---|---|---|
| 5,202,297 A * | 4/1993 | Lorz | ..................... | C07F 15/008 502/161 |
| 5,512,695 A * | 4/1996 | Kreutzer | ................ | B01J 31/185 502/121 |
| 7,943,801 B2 * | 5/2011 | Choi | ....................... | C07C 45/50 502/152 |
| 2010/0036143 A1 | 2/2010 | Selent et al. | | |

FOREIGN PATENT DOCUMENTS

WO   WO 2008/071508 A1   6/2008
WO   WO 2014/056733 A1   4/2014

OTHER PUBLICATIONS

Extended European Search Report issued May 13, 2015 in Patent Application No. 14196187.0.
Robert Franke, et al., "Applied Hydroformylation" Chemical Reviews, vol. 112, 2012, pp. 5675-5732.

* cited by examiner

*Primary Examiner* — Valerie Rodriguez-Garcia
(74) *Attorney, Agent, or Firm* — Oblon, McClelland, Maier & Neustadt, L.L.P.

(57) ABSTRACT

Bisphosphites having at least one unsymmetric outer biphenol unit are useful for the hydroformylation of an olefin.

5 Claims, 1 Drawing Sheet

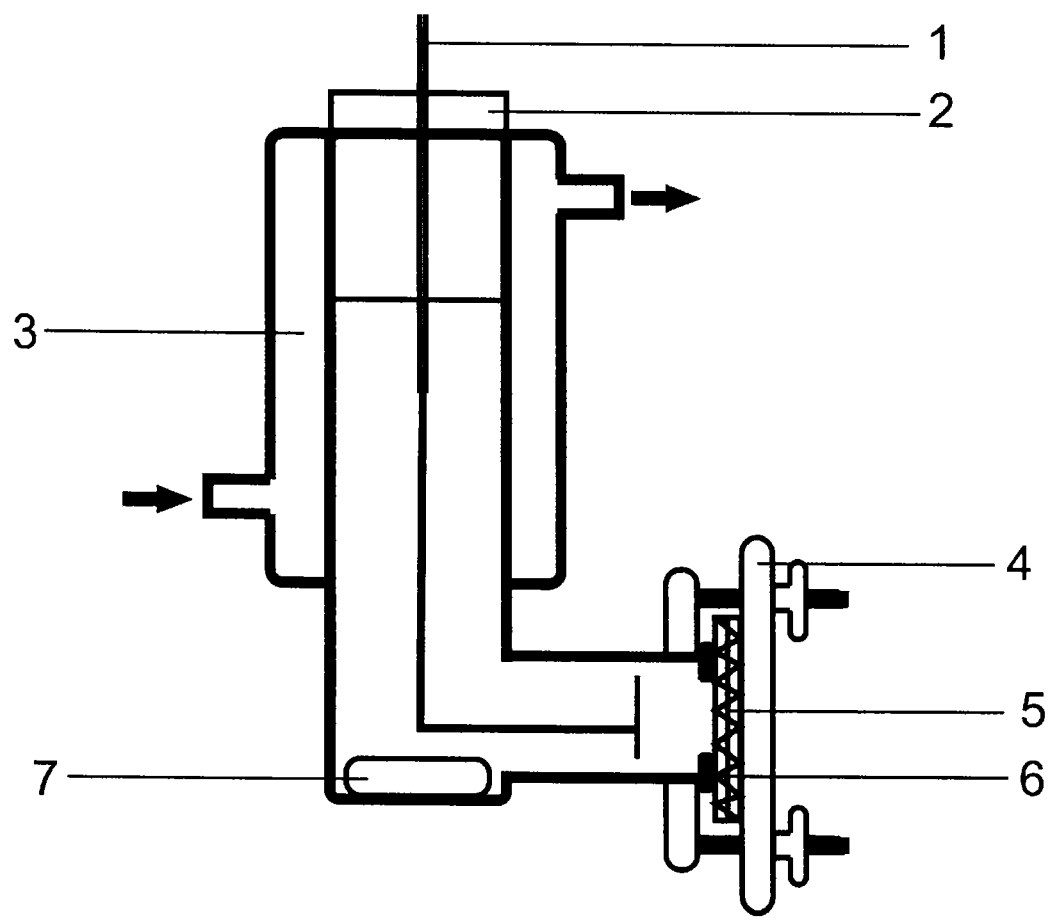

BISPHOSPHITES HAVING AN UNSYMMETRIC OUTER BIPHENOL UNIT

BACKGROUND OF THE INVENTION

Field of the Invention

The invention relates to bisphosphites having at least one unsymmetric outer biphenol unit. In addition, the use thereof as ligands in hydroformylation.

Discussion of the Background

A bisphosphite has a central unit, called the backbone, and two outer units bonded to the central unit via the phosphorus atom. The two outer units here may be the same, or else different.

The reactions between olefin compounds, carbon monoxide and hydrogen in the presence of a catalyst to give the aldehydes comprising one additional carbon atom are known as hydroformylation or oxo synthesis. The catalysts used in these reactions are frequently compounds of the transition metals of group VIII of the Periodic Table of the Elements. Known ligands include, for example, compounds of the phosphine, phosphite and phosphonite classes each comprising trivalent phosphorus $P^{III}$. A good overview of the state of the hydroformylation of olefins can be found in B. CORNILS, W. A. HERRMANN, "Applied Homogeneous Catalysis with Organometallic Compounds", vol. 1 & 2, VCH, Weinheim, N.Y., 1996 or R. Franke, D. Selent, A. Börner, "Applied Hydroformylation", Chem. Rev., 2012, DOI:10.1021/cr3001803.

Every catalytically active composition has its specific benefits. According to the feedstock and target product, therefore, different catalytically active compositions are used.

U.S. Pat. No. 4,694,109 and U.S. Pat. No. 4,879,416 describe bisphosphine ligands and use thereof in the hydroformylation of olefins at low synthesis gas pressures. Particularly in the case of hydroformylation of propene, ligands of this type achieve high activities. WO 95/30680 discloses bidentate phosphine ligands and the use thereof in catalysis, including in hydroformylation reactions.

DE 10 2006 058 682 A1 discloses bisphosphites having different but symmetric outer units, for example compound 1b on page 8 of DE 10 2006 058 682 A1.

Even though a multitude of ligands and the use thereof in rhodium-catalysed hydroformylation are known, it is desirable to develop new ligands having improved properties.

SUMMARY OF THE INVENTION

The problem addressed by the invention was that of providing bisphosphites having advantageous properties in hydroformylation compared to the known bisphosphites. The problem addressed was more particularly that of developing novel ligands, the use of which, as compared with structurally similar bisphosphites likewise having three biphenol units, leads to an improved yield. The improved yield was to be implemented in the case of at least one olefin.

The present invention provides a compound having the general structure I

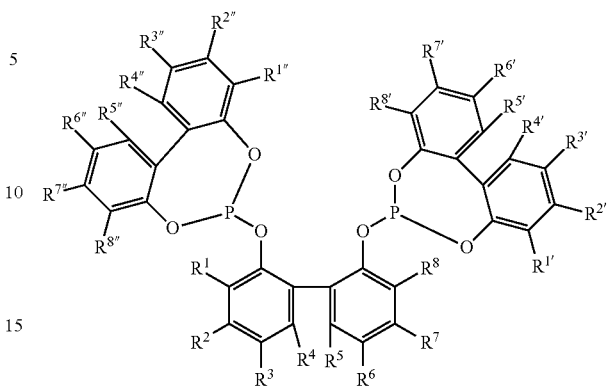

wherein $R^1$, $R^2$, $R^3$, $R^4$, $R^5$, $R^6$, $R^7$, $R^8$ are each independently selected from the group consisting of:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —CN, —$NH_2$, and —N[($C_1$-$C_{12}$)-alkyl]$_2$;

$R^{1'}$, $R^{2'}$, $R^{3'}$, $R^{4'}$, $R^{5'}$, $R^{6'}$, $R^{7'}$, $R^{8'}$, $R^{1''}$, $R^{2''}$, $R^{3''}$, $R^{4''}$, $R^{5''}$, $R^{6''}$, $R^{7''}$, $R^{8''}$ are each independently selected from the group consisting of:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —$NH_2$, and —N[($C_1$-$C_{12}$)-alkyl]$_2$;

wherein the alkyl and aryl groups may be substituted, and two radicals from at least one of the four following pairs of radicals are not the same radical: $R^{1'}$ and $R^{8'}$, $R^{2'}$ and $R^{7'}$, $R^{3'}$ and $R^{6'}$, $R^{4'}$ and $R^{5'}$; and/or two radicals from at least one of the four following pairs of radicals are not the same radical: $R^{1''}$ and $R^{8''}$, $R^{2''}$ and $R^{7''}$, $R^{3''}$ and $R^{6''}$, $R^{4''}$ and $R^{5''}$.

In one embodiment, the invention provides a complex, comprising:

a compound as above; and a metal atom selected from the group consisting of: Rh, Ru, Co, and Ir.

The invention also relates to a catalyst for catalyzing a hydroformylation reaction, comprising: the compound as above.

The invention further relates to a process for hydroformylation of an olefin, comprising:

a) initially charging an olefin into a reactor;

b) adding i) a complex as above;

or ii) a compound as above and a substance having a metal atom selected from the group consisting of: Rh, Ru, Co, and Ir;

c) feeding into said reactor $H_2$ and CO, to obtain a reaction mixture;

d) heating the reaction mixture, to obtain conversion of the olefin to an aldehyde.

BRIEF DESCRIPTION OF DRAWINGS

FIG. 1 shows a reaction apparatus in which a coupling reaction to give unsymmetric biaryls can be conducted.

DETAILED DESCRIPTION OF THE INVENTION

Any ranges mentioned herein below include all values and subvalues between the lowest and highest limit of this range.

The present invention provides for a compound which has the general structure I:

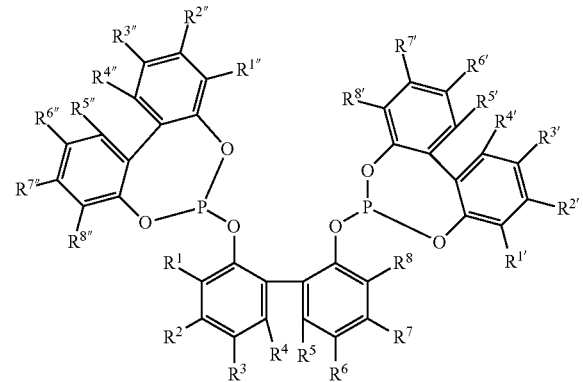

(I)

where $R^1, R^2, R^3, R^4, R^5, R^6, R^7, R^8$ are selected from:

—H, —$(C_1$-$C_{12})$-alkyl, —O—$(C_1$-$C_{12})$-alkyl, —O—$(C_6$-$C_{20})$-aryl, —$(C_6$-$C_{20})$-aryl, —S-alkyl, —S-aryl, halogen, COO—$(C_1$-$C_{12})$-alkyl, CONH—$(C_1$-$C_{12})$-alkyl, —CO—$(C_1$-$C_{12})$-alkyl, —CO—$(C_6$-$C_{20})$-aryl, —COOH, —OH, —$SO_3H$, —CN, —$NH_2$, —N[$(C_1$-$C_{12})$-alkyl]$_2$;

$R^{1'}, R^{2'}, R^{3'}, R^{4'}, R^{5'}, R^{6'}, R^{7'}, R^{8'}, R^{1''}, R^{2''}, R^{3''}, R^{4''}, R^{5''}, R^{6''}, R^{7''}, R^{8''}$ are selected from:

—H, —$(C_1$-$C_{12})$-alkyl, —O—$(C_1$-$C_{12})$-alkyl, —O—$(C_6$-$C_{20})$-aryl, —$(C_6$-$C_{20})$-aryl, —S-alkyl, —S-aryl, halogen, COO—$(C_1$-$C_{12})$-alkyl, CONH—$(C_1$-$C_{12})$-alkyl, —CO—$(C_1$-$C_{12})$-alkyl, —CO—$(C_6$-$C_{20})$-aryl, —COOH, —OH, —$SO_3H$, —$NH_2$, —N[$(C_1$-$C_{12})$-alkyl]$_2$;

where the alkyl and aryl groups mentioned may be substituted, and two radicals from at least one of the four following pairs of radicals are not the same radical: $R^{1'}$ and $R^{8'}$, $R^{2'}$ and $R^{7'}$, $R^{3'}$ and $R^{6'}$, $R^{4'}$ and $R^{5'}$, and/or two radicals from at least one of the four following pairs of radicals are not the same radical: $R^{1''}$ and $R^{8''}$, $R^{2''}$ and $R^{7''}$, $R^{3''}$ and $R^{6''}$, $R^{4''}$ and $R^{5''}$.

The feature "and the two radicals from at least one of the four following pairs of radicals are not the same radical: $R^{1'}$ and $R^{8'}$, $R^{2'}$ and $R^{7'}$, $R^{3'}$ and $R^{6'}$, $R^{4'}$ and $R^{5'}$ and/or the two radicals from at least one of the four following pairs of radicals are not the same radical: $R^{1''}$ and $R^{8''}$, $R^{2''}$ and $R^{7''}$, $R^{3''}$ and $R^{6''}$, $R^{4''}$ and $R^{5''}$ expresses the fact that at least one of the two outer biphenol units is a unsymmetric biphenol. It is also possible that both outer biphenol units at the same time are unsymmetric. In the case of unsymmetric biphenols, the two aromatic systems cannot be imaged over one another by a mirror plane between them.

Examples of permitted radical pairs are as follows:
$R^{1'} \neq R^{8'}$, $R^{2'} = R^{7'}$, $R^{3'} = R^{6'}$, $R^{4'} = R^{5'}$,
$R^{1'} = R^{8'}$, $R^{2'} = R^{7'}$, $R^{3'} \neq R^{6'}$, $R^{4'} = R^{5'}$.

But also radical pairs where more than one pair is non-identical, for example:
$R^{1'} \neq R^{8'}$, $R^{2'} = R^{7'}$, $R^{3'} \neq R^{6'}$, $R^{4'} = R^{5'}$,
$R^{1'} \neq R^{8'}$, $R^{2'} \neq R^{7'}$, $R^{3'} \neq R^{6'}$, $R^{4'} = R^{5'}$.

The only case ruled out is that in which all four pairs of radicals are each the same radical in pairs:
$R^{1'} = R^{8'}$, $R^{2'} = R^{7'}$, $R^{3'} = R^{6'}$, $R^{4'} = R^{5'}$.

This would be a symmetric biphenol.

The same applies analogously to the " radicals.

$(C_1$-$C_{12})$-Alkyl and O—$(C_1$-$C_{12})$-alkyl may each be unsubstituted or substituted by one or more identical or different radicals selected from $(C_3$-$C_{12})$-cycloalkyl, $(C_3$-$C_{12})$-heterocycloalkyl, $(C_6$-$C_{20})$-aryl, fluorine, chlorine, cyano, formyl, acyl and alkoxycarbonyl.

$(C_6$-$C_{20})$-Aryl and —$(C_6$-$C_{20})$-aryl-$(C_6$-$C_{20})$-aryl- may each be unsubstituted or substituted by one or more identical or different radicals selected from:

—H, —O—$(C_1$-$C_{12})$-alkyl, —O—$(C_6$-$C_{20})$-aryl, —$(C_6$-$C_{20})$-aryl, -halogen (such as Cl, F, Br, I), —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_6$-$C_{20})$-aryl, —COOH, —OH, —$SO_3H$, —$SO_3Na$, —$NO_2$, —CN, —$NH_2$, —N[$(C_1$-$C_{12})$-alkyl]$_2$.

In the context of the invention, the expression "—$(C_1$-$C_{12})$-alkyl" encompasses straight-chain and branched alkyl groups. Preferably, these groups are unsubstituted straight-chain or branched —$(C_1$-$C_8)$-alkyl groups and most preferably —$(C_1$-$C_6)$-alkyl groups. Examples of —$(C_1$-$C_{12})$-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression "—$(C_1$-$C_{12})$-alkyl" also apply to the alkyl groups in —O—$(C_1$-$C_{12})$-alkyl, i.e. in —$(C_1$-$C_{12})$-alkoxy. Preferably, these groups are unsubstituted straight-chain or branched —$(C_1$-$C_6)$-alkoxy groups.

Substituted —$(C_1$-$C_{12})$-alkyl groups and substituted —$(C_1$-$C_{12})$-alkoxy groups may have one or more substituents, depending on their chain length. The substituents are preferably each independently selected from —$(C_3$-$C_{12})$-cycloalkyl, —$(C_3$-$C_{12})$-heterocycloalkyl, —$(C_6$-$C_2O$-aryl, fluorine, chlorine, cyano, formyl, acyl and alkoxycarbonyl.

The expression "—$(C_3$-$C_{12})$-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl and adamantyl. One example of a substituted cycloalkyl would be menthyl.

The expression "—$(C_3$-$C_{12})$-heterocycloalkyl groups", in the context of the present invention, encompasses nonaromatic saturated or partly unsaturated cycloaliphatic groups having 3 to 12, especially 5 to 12, carbon atoms. The —$(C_3$-$C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—. Examples of —($C_3$-$C_{12}$)-heterocycloalkyl groups are tetrahydrothiophenyl, tetrahydrofuryl, tetrahydropyranyl and dioxanyl.

In the context of the present invention, the expression "—($C_6$-$C_{20}$)-aryl and —($C_6$-$C_{20}$)-aryl-($C_6$-$C_{20}$)-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —($C_6$-$C_{10}$)-aryl and —($C_6$-$C_{10}$)-aryl-($C_6$-$C_{10}$)-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —($C_6$-$C_{20}$)-aryl groups and —($C_6$-$C_{20}$)-aryl-($C_6$-$C_{20}$)-aryl groups may have one or more (e.g. 1, 2, 3, 4 or 5) substituents, depending on the ring size. These substituents are preferably each independently selected from —H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen (such as Cl, F, Br, I), —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —$SO_3H$, —$SO_3Na$, —$NO_2$, —CN, —$NH_2$, —N[($C_1$-$C_{12}$)-alkyl]$_2$.

Substituted —($C_6$-$C_{20}$)-aryl groups and —($C_6$-$C_{20}$)-aryl-($C_6$-$C_{20}$)-aryl groups are preferably substituted —($C_6$-$C_{10}$)-aryl groups and —($C_6$-$C_{10}$)-aryl-($C_6$-$C_{10}$)-aryl groups, especially substituted phenyl or substituted naphthyl or substituted anthracenyl. Substituted —($C_6$-$C_{20}$)-aryl groups preferably bear one or more, for example 1, 2, 3, 4 or 5, substituents selected from —($C_1$-$C_{12}$)-alkyl groups, —($C_1$-$C_{12}$)-alkoxy groups.

In one embodiment, $R^1$, $R^2$, $R^3$, $R^4$, $R^5$, $R^6$, $R^7$, $R^8$ are selected from:
—H, —($C_1$-$C_{12}$)-alkyl, —O—($C_1$-$C_{12}$)-alkyl, —O—($C_6$-$C_{20}$)-aryl, —S-alkyl, —S-aryl.

In one embodiment, $R^{1\prime}$, $R^{2\prime}$, $R^{3\prime}$, $R^{4\prime}$, $R^{5\prime}$, $R^{6\prime}$, $R^{7\prime}$, $R^{8\prime}$ are selected from:
—H, —($C_1$-$C_{12}$)-alkyl, —O—($C_1$-$C_{12}$)-alkyl, —O—($C_6$-$C_{20}$)-aryl, —S-alkyl, —S-aryl.

In one embodiment, $R^{1\prime\prime}$, $R^{2\prime\prime}$, $R^{3\prime\prime}$, $R^{4\prime\prime}$, $R^{5\prime\prime}$, $R^{6\prime\prime}$, $R^{7\prime\prime}$, $R^{8\prime\prime}$ are selected from:
—H, —($C_1$-$C_{12}$)-alkyl, —O—($C_1$-$C_{12}$)-alkyl, —O—($C_6$-$C_{20}$)-aryl, —S-alkyl, —S-aryl.

In one embodiment, $R^1$, $R^2$, $R^3$, $R^4$, $R^5$, $R^6$, $R^7$, $R^8$ are selected from:
—H, —($C_1$-$C_{12}$)-alkyl, —O—($C_1$-$C_{12}$)-alkyl, —O—($C_6$-$C_{20}$)-aryl.

In one embodiment, $R^{1\prime}$, $R^{2\prime}$, $R^{3\prime}$, $R^{4\prime}$, $R^{5\prime}$, $R^{6\prime}$, $R^{7\prime}$, $R^{8\prime}$ are selected from:
—H, —($C_1$-$C_{12}$)-alkyl, —O—($C_1$-$C_{12}$)-alkyl, —O—($C_6$-$C_{20}$)-aryl.

In one embodiment, $R^{1\prime\prime}$, $R^{2\prime\prime}$, $R^{3\prime\prime}$, $R^{4\prime\prime}$, $R^{5\prime\prime}$, $R^{6\prime\prime}$, $R^{7\prime\prime}$, $R^{8\prime\prime}$ are selected from:
—H, —($C_1$-$C_{12}$)-alkyl, —O—($C_1$-$C_{12}$)-alkyl, —O—($C_6$-$C_{20}$)-aryl.

In one embodiment, $R^1$, $R^{1\prime}$ and $R^{1\prime\prime}$ are the same radical and $R^8$, $R^{8\prime}$ and $R^{8\prime\prime}$ are the same radical.

In one embodiment, $R^{1\prime}$ and $R^{8\prime}$ are not the same radical and
$R^{1\prime\prime}$ and $R^{8\prime\prime}$ are not the same radical.

In one embodiment, the two radicals from at least one of the four following pairs of radicals are not the same radical: $R^{1\prime}$ and $R^{8\prime}$, $R^{2\prime}$ and $R^{7\prime}$, $R^{3\prime}$ and $R^{6\prime}$, $R^{4\prime}$ and $R^{5\prime}$, and the two radicals from at least one of the four following pairs of radicals are not the same radical: $R^{1\prime\prime}$ and $R^{8\prime\prime}$, $R^{2\prime\prime}$ and $R^{7\prime\prime}$, $R^{3\prime\prime}$ and $R^{6\prime\prime}$, $R^{4\prime\prime}$ and $R^{5\prime\prime}$.

In one embodiment, the two radicals from at least one of the four following pairs of radicals are not the same radical: $R^{1\prime}$ and $R^{8\prime}$, $R^{2\prime}$ and $R^{7\prime}$, $R^{3\prime}$ and $R^{6\prime}$, $R^{4\prime}$ and $R^{5\prime}$, and the two radicals from at least one of the four following pairs of radicals are the same radical: $R^{1\prime\prime}$ and $R^{8\prime\prime}$, $R^{2\prime\prime}$ and $R^{7\prime\prime}$, $R^{3\prime\prime}$ and $R^{6\prime\prime}$, $R^{4\prime\prime}$ and $R^{5\prime\prime}$.

In one embodiment, at least one of the four radicals mentioned is different from the other radicals: $R^{1\prime}$, $R^{8\prime}$, $R^{1\prime\prime}$, $R^{8\prime\prime}$.

In one embodiment, at least one of the four radicals mentioned is different from the other radicals: $R^{2\prime}$, $R^{7\prime}$, $R^{2\prime\prime}$, $R^{7\prime\prime}$.

In one embodiment, at least one of the four radicals mentioned is different from the other radicals: $R^{3\prime}$, $R^{6\prime}$, $R^{3\prime\prime}$, $R^{6\prime\prime}$.

In one embodiment, at least one of the four radicals mentioned is different from the other radicals: $R^{4\prime}$, $R^{5\prime}$, $R^{4\prime\prime}$, $R^{5\prime\prime}$.

In one embodiment, the three radicals in the following groups of three are each the same radical:
$R^1=R^{1\prime}=R^{1\prime\prime}$,
$R^2=R^{2\prime}=R^{2\prime\prime}$,
$R^3=R^{3\prime}=R^{3\prime\prime}$,
$R^4=R^{4\prime}=R^{4\prime\prime}$,
$R^5=R^{5\prime}=R^{5\prime\prime}$,
$R^6=R^{6\prime}=R^{6\prime\prime}$.

In one embodiment, the compound has the formula (1):

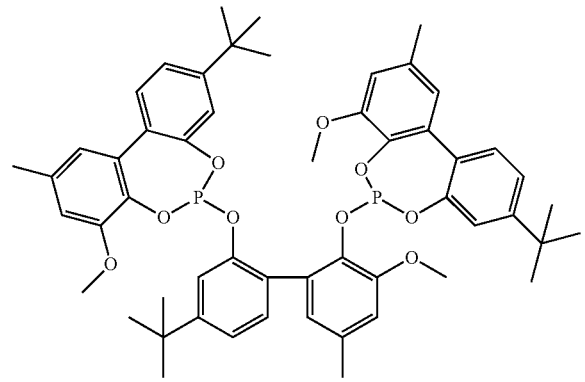

(1)

As well as the compounds, also claimed is a complex comprising these compounds.

Complex comprising:
a compound described above,
a metal atom selected from: Rh, Ru, Co, Ir.

In a preferred embodiment, the metal is Rh.

In this regard, see R. Franke, D. Selent, A. Börner, "Applied Hydroformylation", Chem. Rev., 2012, DOI: 10.1021/cr3001803; p. 5688, Scheme 12 "General Method for the Preparation of a P-Modified Rh precatalyst" and references cited therein, and also P. W. N. M. van Leeuwen, in Rhodium Catalyzed Hydroformylation, P. W. N. M. van Leeuwen, C. Claver (eds.), Kluwer, Dordrecht, 2000, inter alia p. 48 ff., p. 233 ff. and references cited therein, and also K. D. Wiese and D. Obst in Top. Organomet. Chem. 2006, 18, 1-13; Springer Verlag Berlin Heidelberg 2006 p. 6 ff. and references cited therein.

Additionally claimed is the use of the compound as ligand in a ligand-metal complex for catalysis of a hydroformylation reaction.

Use of a compound described above in a ligand-metal complex for catalysis of a hydroformylation reaction.

The process in which the compound is used as ligand in a ligand-metal complex for conversion of an olefin to an aldehyde is likewise claimed.

A process comprising the following process steps:
a) initially charging an olefin,
b) adding an above-described complex,
or an above-described compound and a substance including a metal atom selected from: Rh, Ru, Co, Ir,
c) feeding in $H_2$ and CO,
d) heating the reaction mixture, with conversion of the olefin to an aldehyde.

In this process, process steps a) to d) can be effected in any desired sequence.

An excess of ligands can also be used in this case and each ligand is not necessarily present bound in the form of a ligand-metal complex but is present as free ligand in the reaction mixture.

The reaction is conducted under customary conditions. Preference is given to a temperature of 80° C. to 160° C. and a pressure of 1 bar to 300 bar.

Particular preference is given to a temperature of 100° C. to 160° C. and a pressure of 15 bar to 250 bar.

The reactants for the hydroformylation in the process of the invention are olefins or mixtures of olefins, especially monoolefins having 2 to 24, preferably 3 to 16 and more preferably 3 to 12 carbon atoms, having terminal or internal C—C double bonds, for example 1-propene, 1- or 2-pentene, 2-methyl-1-butene, 2-methyl-2-butene, 3-methyl-1-butene, 1-, 2- or 3-hexene, the $C_6$ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl-2-heptene, 2-ethyl-1-hexene, the $C_8$ olefin mixture obtained in the dimerization of butenes (dibutene), nonenes, 2- or 3-methyloctenes, the $C_9$ olefin mixture obtained in the trimerization of propene (tripropene), decenes, 2-ethyl-1-octene, dodecenes, the $C_{12}$ olefin mixture obtained in the tetramerization or the trimerization of butenes (tetrapropene or tributene), tetradecenes, hexadecenes, the $C_{16}$ olefin mixture obtained in the tetramerization of butenes (tetrabutane), and olefin mixtures prepared by cooligomerization of olefins having different numbers of carbon atoms (preferably 2 to 4).

Having generally described this invention, a further understanding can be obtained by reference to certain specific examples which are provided herein for purposes of illustration only, and are not intended to be limiting unless otherwise specified.

EXAMPLES

The invention is illustrated in detail hereinafter by working examples and a FIGURE.

FIG. 1 shows a reaction apparatus in which the coupling reaction to give the corresponding unsymmetric biaryls can be conducted. The apparatus comprises a nickel cathode (1) and an anode composed of boron-doped diamond (BDD) on silicon (5). The apparatus can be cooled with the aid of a cooling jacket (3). The arrows indicate the flow direction of the cooling water. The reaction space is sealed by a Teflon stopper (2). The reaction mixture is mixed by a magnetic stirrer bar (7). On the anodic side, the apparatus is sealed by screw clamps (4) and seals (6).

Analysis

Chromatography

The preparative liquid chromatography separations via flash chromatography were conducted with a maximum pressure of 1.6 bar on 60 M silica gel (0.040-0.063 mm) from Macherey-Nagel GmbH & Co, Duren. The unpressurized separations were conducted on Geduran Si 60 silica gel (0.063-0.200 mm) from Merck KGaA, Darmstadt. The solvents used as eluents (ethyl acetate (technical grade), cyclohexane (technical grade)) had been purified by distillation beforehand on a rotary evaporator.

For thin-film chromatography (TLC), ready-made PSC silica gel 60 F254 plates from Merck KGaA, Darmstadt were used. The Rf values are reported as a function of the eluent mixture used. The TLC plates were stained using a cerium/molybdatophosphoric acid solution as immersion reagent. Cerium/molybdatophosphoric acid reagent: 5.6 g of molybdatophosphoric acid, 2.2 g of cerium(IV) sulphate tetrahydrate and 13.3 g of concentrated sulphuric acid to 200 ml of water.

Gas Chromatography (GC/GCMS)

The gas chromatography studies (GC) on product mixtures and pure substances were effected with the aid of the GC-2010 gas chromatograph from Shimadzu, Japan. Analysis is effected on an HP-5 quartz capillary column from Agilent Technologies, USA (length: 30 m; internal diameter: 0.25 mm; film thickness of the covalently bound stationary phase: 0.25 μm; carrier gas: hydrogen; injector temperature: 250° C.; detector temperature: 310° C.; programme: "hard" method: start temperature 50° C. for 1 min, heating rate: 15° C./min, end temperature 290° C. for 8 min). Gas chromatography-mass spectrometry analyses (GC-MS) of product mixtures and pure substances were recorded with the aid of the GC-2010 gas chromatograph combined with the GCMS-QP2010 mass detector from Shimadzu, Japan. Analysis is effected on an HP-1 quartz capillary column from Agilent Technologies, USA (length: 30 m; internal diameter: 0.25 mm; film thickness of the covalently bound stationary phase: 0.25 μm; carrier gas: hydrogen; injector temperature: 250° C.; detector temperature: 310° C.; programme: "hard" method: start temperature 50° C. for 1 min, heating rate: 15° C./min, end temperature 290° C. for 8 min; GC-MS: ion source temperature: 200° C.).

Melting Points

Melting points were measured with the aid of the SG 2000 melting point determination instrument from HW5, Mainz, and are uncorrected.

Elemental Analysis

The elemental analyses were conducted in the analytical division of the Organic Chemistry department of the Johannes Gutenberg University of Mainz on a Vario EL Cube from Foss-Heraeus, Hanau.

Mass Spectrometry

All electrospray ionization analyses (ESI+) were conducted on a QTof Ultima 3 from Waters Micromasses, Milford, Mass. EI mass spectra and the high-resolution EI spectra were analysed on an instrument of the MAT 95 XL sector field instrument type from ThermoFinnigan, Bremen.

NMR Spectroscopy

The NMR spectroscopy studies were conducted on multinucleus resonance spectrometers of the AC 300 or AV II 400 type from Bruker, Analytische Messtechnik, Karlsruhe. The solvent used was CDCl3. The 1H and 13C spectra were calibrated according to the residual content of undeuterated solvent using the NMR Solvent Data Chart from Cambridge Isotopes Laboratories, USA. Some of the 1H and 13C signals were assigned with the aid of H,H-COSY, H,H-

NOESY, H,C-HSQC and H,C-HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported in hertz (Hz) together with the number of bonds covered. The numbering given in the assignment of signals corresponds to the numbering shown in the formula schemes, which do not necessarily have to correspond to IUPAC nomenclature.

General Operating Procedures

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Synthesis of Unsymmetric Biphenols

The unsymmetric biphenols were prepared by an electrochemical method by coupling two phenols which differ in terms of oxidation potential. In this regard, see also B. Elsler, D. Schollmeyer, K. M. Dyballa, R. Franke, S. R. Waldvogel, "Metall- and reagensfreie hochselektive anodische Kreuzkupplung von Phenolen" [Metal- and Reagent-Free High-Selectivity Anodic Cross-Coupling of Phenols], Angew. Chem., 2014, DOI: 10.1002/ange.201400627

General Procedure:

The coupling reaction was conducted in an apparatus as shown in FIG. 1.

5 mmol of the first phenol having an oxidation potential $E_{Ox}1$ together with 15 mmol of the second phenol having an oxidation potential $E_{Ox}2$ are dissolved in 1,1,1,3,3,3-hexafluoroisopropanol (HFIP) and MeOH or in formic acid and MeOH in the amounts specified in Table 1 below. The electrolysis is galvanostatic. The outer shell of the electrolysis cell is kept at a controlled temperature of about 10° C. by means of a thermostat, while the reaction mixture is stirred and heated to 50° C. with the aid of a sand bath. After the electrolysis has ended, the cell contents are transferred together with toluene to a 50 ml round-bottom flask and the solvent is removed on a rotary evaporator at 50° C., 200-70 mbar, under reduced pressure. Unconverted reactant is recovered by means of short-path distillation (100° C., $10^{-3}$ mbar).

Electrode material

Anode: boron-doped diamond (BDD) on Si

Cathode: Ni mesh

Electrolysis conditions:

| Temperature [T]: | 50° C. |
| --- | --- |
| Current [I]: | 15 mA |
| Current density [j]: | 2.8 mA/cm² |
| Charge [Q]: | 2 F/mol of deficiency component |
| Terminal voltage [$U_{max}$]: | 3-5 V |

The biphenols were synthesized by the general method described above, and in a reaction apparatus as shown in FIG. 1.

2,2'-Dihydroxy-3-methoxy-5-methyl-4'-(dimethylethyl)biphenyl

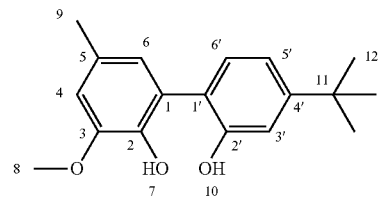 [SMILES: COc1cc(C)cc(-c2ccc(C(C)(C)C)cc2O)c1O]

0.69 g (5 mmol, 1.0 equiv.) of 4-methylguaiacol and 2.25 g (15 mmol, 3.0 equiv.) of 3-tert-butylphenol were dissolved in 33 ml of 1,1,1,3,3,3-hexafluoroisopropanol (HFIP), 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a colourless solid.

Yield: 808 mg (63%, 3.1 mmol)

GC (hard method, HP-5): $t_R$=13.97 min $R_f$(CH:EA=4:1)=0.29

$m_p$=160.3° C. (recrystallized from DCM/CH)

$^1$H NMR (400 MHz, CDCl$_3$) δ=1.37 (s, 9H, 12-H), 2.36 (s, 3H, 9-H), 3.94 (s, 3H, 8-H), 6.25 (s, 1H, 7-H), 6.48 (s, 1H, 10-H), 6.75 (d, 1H, 6-H), 6.79 (d, 1H, 4-H), 7.08 (dd, 1H, 5'-H), 7.12 (d, 1H, 3'-H), 7.27 (d, 1H, 6'-H);

Couplings: $^4J_{4-H, 6-H}$=1.7 Hz; $^3J_{5'-H, 6'-H}$=8.0 Hz, $^4J_{3'-H, 5'-H}$=1.7 Hz;

$^{13}$C NMR (101 MHz, CDCl$_3$) δ=21.24 (C-9), 31.31 (C-12), 34.58 (C-11), 56.15 (C-8), 110.79 (C-4), 114.94 (C-3'), 118.30 (C-5'), 122.37 (C-F), 123.88 (C-1), 123.94 (C-6), 130.45 (C-6'), 130.53 (C-4'), 139.24 (C-5), 146.32 (C-3), 152.91 (C-2'), 153.13 (C-2).

HRMS for C$_{15}$H$_{16}$O$_4$ (ESI+) [M+Na$^+$]: calc: 309.1467, found: 309.1466.

MS (EI, GCMS): m/z (%): 242 (100) [M]$^+$, 227 (38) [M-CH$_3$]$^+$.

Elemental analysis for C$_{18}$H$_{22}$O$_3$: calc: 75.50%, H, 7.74%, found: C, 75.41%, H, 7.72%.

Synthesis of the Ligands 6,6'-((4'-(tert-Butyl)-3-methoxy-5-methyl-[1,1'-biphenyl]-2,2'-diyl)bis(oxy))bis(9-(tert-butyl)-4-methoxy-2-methyldibenzo[d,f]1,3,2]dioxaphosphepin)

(1)

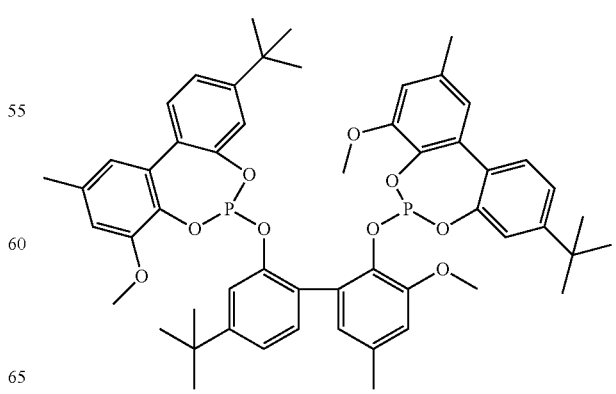

A solution of 4'-(tert-butyl)-3-methoxy-5-methyl-[1,1'-biphenyl]-2,2'-diol (0.274 g; 0.957 mmol) in THF (10 ml) was admixed with a solution of two equivalents of n-butyllithium in hexane (3.59 ml) at −20° C., the mixture obtained was stirred at this temperature for another 20 min and then a solution of 9-(tert-butyl)-6-chloro-4-methoxy-2-methyl-dibenzo[d,f][1,3,2]dioxaphosphepin (0.792 g; 2.258 mmol) in THF (11 ml) was added at room temperature. The reaction mixture was stirred overnight and the solvent was removed under reduced pressure. Toluene (25 ml) was added and the resulting suspension was filtered. The filtrate was filtered once again through silica gel and the solvent was removed under reduced pressure. The resultant solid was dried at 50° C./0.1 mbar for 3 h. Yield: 0.856 g (0.936 mmol; 98%).

Elemental analysis (calc. for $C_{54}H_{60}O_9P_2$=915.01 g/mol) C, 70.67 (70.88); H, 6.52 (6.61); P, 6.69 (6.77) %.

$^{31}$P NMR ($CD_2Cl_2$): 141.9 (d, $J_{PP}$=7.8 Hz); 142.2 (d, $J_{PP}$=7.8 Hz); 145.1 (d, $J_{PP}$=7.8 Hz); 145.2 (d, $J_{PP}$=7.8 Hz) ppm.

$^1$H NMR ($CD_2Cl_2$): 1.22-1.33 (dd, 18 H); 1.37 (m, 9 H); 2.42 (m, 9 H); 3.81-3.88 (dd, 6 H); 4.02 (s, 3 H); 6.79-6.85 (m, 3H, $H_{arom}$); 6.88 (m, 2 H, $H_{arom}$); 6.90-6.98 (m, 1 H, $H_{arom}$); 6.95 (m, 1 H, $H_{arom}$); 7.00-7.05 (m, 1 H, $H_{arom}$); 7.20-7.35 (m, 4 H, $H_{arom}$); 7.37-7.44 (m, 3 H, $H_{arom}$) ppm.

6,6'((4'-(tert-Butyl)-3-methoxy-5-methyl-[1,1'-biphenyl]-2,2'-diyl)bis(oxy))didibenzo[d,f][1,3,2]dioxaphosphepin

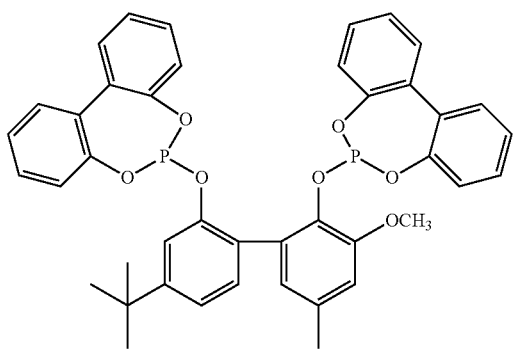

(2)

A solution of 4'-(tert-butyl)-3-methoxy-5-methyl-[1,1'-biphenyl]-2,2'-diol (0.489 g; 1.708 mmol) in toluene (12 ml) was admixed with pyridine (0.389 g; 3.844 mmol) and the resultant mixture was added dropwise at 3° C. to a solution of 6-chlorodibenzo[d,f][1,3,2]dioxaphosphepin (0.942 g; 3.758 mmol) in toluene (12 ml). The reaction mixture was stirred overnight and then filtered. The filtrate was concentrated to dryness under reduced pressure and the resultant solid was dried at 50° C./0.1 mbar. The remaining substance was purified by column chromatography (hexane/toluene, 1:2, $R_f$=0.3). Yield: 0.738 g (1.032 mmol; 58%).

Elemental analysis (calc. for $C_{42}H_{36}O_7P_2$=714.69 g/mol) C, 70.59 (70.58); H, 5.28 (5.08); P, 8.85 (8.67) %.

$^{31}$P NMR ($CD_2Cl_2$): 144.3 (d, $J_{PP}$=9.1 Hz); 148.1 (d, $J_{PP}$=9.1 Hz) ppm.

$^1$H NMR ($CD_2Cl_2$): 1.51 (m, 9 H); 2.45 (m, 3 H); 4.06 (s, 3 H); 6.80-6.87 (m, 3H, $H_{arom}$); 6.98-7.03 (m, 2 H, $H_{arom}$); 7.03-7.05 (m, 1 H, $H_{arom}$); 7.28-7.35 (m, 8 H, $H_{arom}$); 7.35-7.38 (m, 1 H, $H_{arom}$); 7.38-7.43 (m, 2 H, $H_{arom}$); 7.46-7.54 (m, 4 H, $H_{arom}$) ppm.

$^{13}$C NMR ($CD_2Cl_2$): 21.5; 57.0; 113.8; 118.4 (d, $J_{CP}$=10.1 Hz); 121.8; 122.5 (d, $J_{CP}$=14.1 Hz); 124.9; 125.5 (d, $J_{CP}$=17.3 Hz); 127.9; 128.7; 129.4; 129.4 (d, $J_{CP}$=16.8 Hz); 130.1 (d, $J_{CP}$=16.1 Hz); 131.3; 131.5; 131.6; 132.0; 134.4; 138.0; 149.5 (d, $J_{CP}$=4.8 Hz); 149.7 (d, $J_{CP}$=4.4 Hz); 149.8 (d, $J_{CP}$=7.0 Hz); 151.2 (d, $J_{CP}$=3.2 Hz); 153.4 ppm.

Procedure for the Catalysis Experiments

The hydroformylation was conducted in a 200 ml autoclave equipped with pressure-retaining valve, gas flow meter, sparging stirrer and pressure pipette from Premex Reactor AG, Lengau, Switzerland. To minimize the influence of moisture and oxygen, the toluene used as solvent was dried with sodium ketyl and distilled under argon. The following substrates used as substrate were heated at reflux over sodium and distilled under argon for several hours: 1-octene (Aldrich), cis/trans-2-pentene (Aldrich) and n-octenes (Oxeno GmbH, octene isomer mixture of 1-octene: ~3%; cis+trans-2-octene; ~49%; cis+trans-3-octene: ~29%; cis+trans-octene-4: ~16%; structurally isomeric octenes: ~3%).

For the experiments, the following solutions of rhodium in the form of [(acac)Rh(COD)] (acac=acetylacetonate anion; COD=1,5-cyclooctadiene) (OMG AG & Co. KG, Hanau, DE) as the catalyst precursor were introduced into the autoclave in toluene under an argon atmosphere: for experiments at 100 ppm by mass of rhodium 10 ml of a 4.31 millimolar solution, for 40 ppm by mass the same amount of an appropriately diluted solution. The appropriate amount of the phosphite compound, generally 2 to 5 ligand equivalents per unit rhodium, dissolved in toluene was then added. By adding further toluene (the total mass of toluene was determined for the GC analysis, see below), the starting volume of the catalyst solution was adjusted to a) 41.0 ml in the case of intended addition of 15 ml of the olefin via the pressure pipette (1-octene, n-octenes and experiments with elevated 2-pentene concentration), or b) 51.9 ml in the case of intended addition of 4.1 ml of 2-pentene. The mass of toluene introduced was determined in each case. Starting weights of the olefins: 1-octene (10.62 g; 94.64 mmol), n-octenes (10.70 g; 95.35 mmol), 2-pentene 9.75 g; 139.00 mmol. The autoclave was heated while stirring (1500 rpm) to the temperatures stated in each case at a total gas pressure (synthesis gas: Linde; $H_2$ (99.999%): CO (99.997%)=1:1) of a) 42 bar for a final pressure of 50 bar; b) 12 bar for a final pressure of 20 bar and c) 7 bar for a final pressure of 10 bar. After reaching the reaction temperature, the synthesis gas pressure was increased to a) 48.5 bar for a final pressure of 50 bar, b) 19.5 bar for a final pressure of 20 bar and c) 9.5 bar for a final pressure of 10 bar and the olefin (mixture) specified in the table in each case was injected under a positive pressure of about 3 bar set in the pressure pipette. The reaction was conducted at a constant pressure of 50, 20 or 10 bar (closed-loop pressure controller from Bronkhorst, the Netherlands) over 4 h. After the reaction time had elapsed, the autoclave was cooled to room temperature, decompressed while stirring and purged with argon. 1 ml of each reaction mixture was removed immediately after the stirrer had been switched off, diluted with 5 ml of pentane and analysed by gas chromatography: HP 5890 Series II plus, PONA, 50 m×0.2 mm×0.5 μm; residual olefin and aldehyde were determined quantitatively against the toluene solvent as internal standard.

Results of the catalysis experiments
Solvent: toluene
Yld.=yield
p=pressure in [bar]
T=temperature in [° C.]

t=time in [h]
[Rh]=rhodium concentration in [ppm]
L/Rh=ratio of ligand to rhodium
The comparative ligand used was the ligand 2.

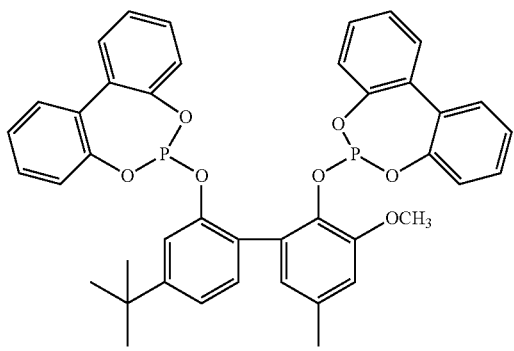

(2)

The inventive compound is identified by *.

TABLE 1

| | | | 1-Octene | | | |
|---|---|---|---|---|---|---|
| Ligand | p (bar) | T (° C.) | t (h) | [Rh] (ppm) | L/Rh | Yld. (%) |
| 1* | 50 | 100 | 4 | 40 | 2 | 91 |
| 2 | 50 | 100 | 4 | 40 | 2 | 90 |

As can be inferred from Table 1, the already very good yield of ligand 2 can be increased once again.

TABLE 2

| | | | 2-Pentene | | | |
|---|---|---|---|---|---|---|
| Ligand | p (bar) | T (° C.) | t (h) | [Rh] (ppm) | L/Rh | Yld. (%) |
| 1* | 20 | 120 | 4 | 100 | 2 | 98 |
| 2 | 20 | 120 | 4 | 100 | 2 | 93 |

As can be inferred from Table 2, the already very good yield of ligand 2 can be increased markedly once again.

As the experimental results show, the stated problem is solved by the inventive compounds.

It has been possible for the first time to generate a bisphosphite which has an unsymmetric outer biphenol unit and has very good hydroformylation properties.

Such specific structures and ligands of this kind were entirely unknown and unobtainable to date.

These bisphosphites have novel asymmetry. The special feature here is the asymmetry within the outer biphenol unit, which leads to unsymmetric bisphosphites. These unsymmetric bisphosphites are thus structurally entirely different from the bisphosphites described in the related art, in which unsymmetric bisphosphite ligands are generated via a particular arrangement of symmetric biphenol units, for example in that the two outer units differ, but the individual units (central unit and outer units) are symmetric per se.

European patent application EP14196187.0 filed Dec. 4, 2014, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A compound represented by structure I:

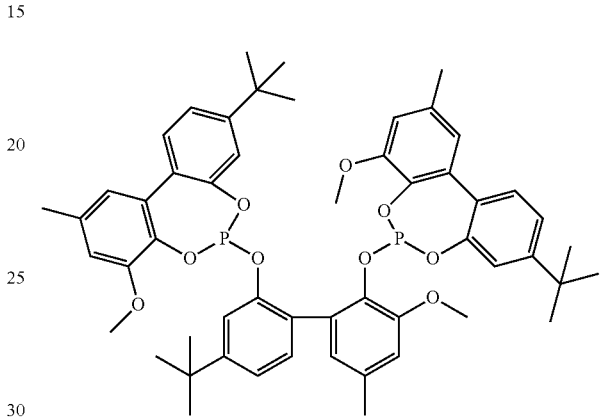

2. A complex, comprising:
a compound according to claim 1; and
a metal atom selected from the group consisting of: Rh, Ru, Co, and Ir.

3. A catalyst for catalyzing a hydroformylation reaction, comprising the compound according to claim 1.

4. A process for hydroformylation of an olefin, comprising:
a) initially charging an olefin into a reactor;
b) a complex according to claim 2 to the reactor;
c) feeding into said reactor $H_2$ and CO, to obtain a reaction mixture; and
d) heating the reaction mixture, to obtain conversion of the olefin to an aldehyde.

5. A process for hydroformylation of an olefin, comprising:
a) initially charging an olefin into a reactor;
b) adding a compound according to claim 1 and a substance having a metal atom selected from the group consistining of: Rh, Ru, Co, and Ir to the reactor;
c) feeding into said reactor $H_2$ and CO, to obtain a reaction mixture; and
d) heating the reaction mixture, to obtain conversion of the olefin to an aldehyde.

* * * * *